(12) United States Patent
Beeckler et al.

(10) Patent No.: US 12,161,395 B2
(45) Date of Patent: *Dec. 10, 2024

(54) CATHETER WITH ANGLED IRRIGATION HOLES

(71) Applicant: Biosense Webster (Israel) Ltd., Yokneam (IL)

(72) Inventors: Christopher Thomas Beeckler, Brea, CA (US); Joseph Thomas Keyes, Sierra Madre, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 677 days.

This patent is subject to a terminal disclaimer.

(21) Appl. No.: 17/335,029

(22) Filed: May 31, 2021

(65) Prior Publication Data

US 2021/0282848 A1    Sep. 16, 2021

Related U.S. Application Data

(63) Continuation of application No. 15/295,296, filed on Oct. 17, 2016, now Pat. No. 11,020,174.

(51) Int. Cl.
*A61B 18/14* (2006.01)
*A61B 18/00* (2006.01)

(52) U.S. Cl.
CPC ............... *A61B 18/1492* (2013.01); *A61B 2018/00351* (2013.01); *A61B 2018/00577* (2013.01); *A61B 2218/002* (2013.01); *A61B 2218/007* (2013.01)

(58) Field of Classification Search
CPC ...... A61B 18/1492; A61B 2018/00011; A61B 2018/00351; A61B 2018/00577;
(Continued)

(56) References Cited

U.S. PATENT DOCUMENTS 6,226,542 B1    5/2001  Reisfeld
6,301,496 B1    10/2001 Reisfeld
(Continued)

FOREIGN PATENT DOCUMENTS

| CN | 103181820 A | 7/2013 |
| CN | 104042331 A | 9/2014 |
| EP | 2913017 A1 | 9/2015 |

OTHER PUBLICATIONS

Extended European Search Report from corresponding EP Application No. 17196531.2 dated Feb. 14, 2018.
(Continued)

*Primary Examiner* — Tigist S Demie
(74) *Attorney, Agent, or Firm* — Troutman Pepper Hamilton Sanders LLP

(57) ABSTRACT

A medical probe for insertion has at least one distal electrode coupled to an energy source to apply energy to tissue inside the body. A plurality of apertures are formed in the electrode. A fluid-directing assembly is disposed in the distal section of the probe having an axial channel that is in fluid communication with at least one trans-axial channel disposed at right angles to the axial channel and leading to an exterior of the assembly. A blocking terminus is disposed forward of the at least one trans-axial channel that prevents irrigation fluid from flowing axially in a forward direction so that the fluid flows outwardly into the lumen of the electrode in at least one trans-axial direction.

14 Claims, 8 Drawing Sheets

(58) Field of Classification Search
CPC .... A61B 2018/00839; A61B 2218/002; A61B 2218/007
See application file for complete search history.

(56) References Cited

U.S. PATENT DOCUMENTS

| | | |
|---|---|---|
| 6,814,733 B2 | 11/2004 | Schwartz et al. |
| 6,893,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 8,517,999 B2 | 8/2013 | Pappone et al. |
| 8,597,238 B2 | 12/2013 | Bonnette et al. |
| 2007/0270791 A1* | 11/2007 | Wang .................... A61B 18/148 606/41 |
| 2008/0161797 A1* | 7/2008 | Wang ..................... A61B 18/14 606/41 |
| 2009/0125016 A1 | 5/2009 | Wang et al. |
| 2010/0152731 A1 | 6/2010 | de la Rama et al. |
| 2011/0009857 A1 | 1/2011 | Subramaniam et al. |
| 2011/0257649 A1 | 10/2011 | Geistert et al. |
| 2012/0157890 A1 | 6/2012 | Govari et al. |
| 2013/0150805 A1 | 6/2013 | Boomsma et al. |
| 2013/0267891 A1 | 10/2013 | Malhi et al. |
| 2014/0257282 A1 | 9/2014 | Wang et al. |
| 2014/0276758 A1 | 9/2014 | Lawrence et al. |
| 2014/0276759 A1* | 9/2014 | Kim .................. A61B 18/1492 606/33 |
| 2015/0272667 A1 | 10/2015 | Govari et al. |
| 2015/0272669 A1 | 10/2015 | Brucker et al. |
| 2017/0079738 A1 | 3/2017 | Botzer et al. |

OTHER PUBLICATIONS

Notification of Reasons for Refusal from corresponding JP Application No. 2017-200129 dated Aug. 31, 2021.
First OA from corresponding CN Application No. 201710977646.9 dated Nov. 19, 2021.
Extended European Search Report from corresponding EP Application No. 22180671.4 dated Jul. 6, 2022.
English translation of Written Opinion dated Mar. 4, 2022, from corresponding Japanese Application No. JP2017-200129.
English translation of Decision to Grant Patent dated Aug. 2, 2022, from corresponding Japanese Application No. JP2017-200129.

* cited by examiner

CATHETER WITH ANGLED IRRIGATION HOLES

PRIORITY CLAIM AND COPYRIGHT NOTICE

This continuation patent application claims the benefits of priority under 35 USC § 120 to prior filed U.S. patent application Ser. No. 15/295,296 filed on Oct. 17, 2016, NOW ALLOWED, which prior patent application is hereby incorporated by reference herein to this application as if set out in full herein. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to devices that introduce media into the body. More particularly, this invention relates to an ablation catheter having side holes for passage of fluid therethrough.

2. Description of the Related Art

In some medical procedures, energy is imparted to body tissue locally, in a concentrated dose, and it is desirable to cool the treatment area in order to reduce collateral tissue damage.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects, coagulum, and or steam pops due to overheating. Such overheated areas can develop high impedance, and may form a functional barrier to the passage of heat. The use of slower heating provides better control of the ablation, but unduly prolongs the procedure.

It has been found that cooling the area of the ablation site reduces tissue charring and thrombus formation. For this purpose, Biosense Webster Inc. (Diamond Bar, California) offers the ThermoCool® irrigated-tip catheter as part of its integrated ablation system. The metal catheter tip, which is energized with RF current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue.

For example, U.S. Pat. No. 8,517,999 to Pappone et al., describes an irrigated catheter With uniform cooling and/or uniform fluid distribution in longitudinally spaced apart elution holes by varying the diameter of a fluid delivery lumen. A number of elution holes are provided in a tip region of a catheter body, and these elution holes are in fluid communication with the lumen through ducts.

SUMMARY OF THE INVENTION

During an ablation procedure there is a concern that blood clots may form. Irrigation reduces the probability of clotting. However, with present catheter distal ends, there are one or more "blind regions" surrounding the end, particularly in the region "behind" the end. In these regions there is little or no irrigation.

There is provided according to embodiments of the invention a medical apparatus, including a probe for insertion into a body of a subject, at least one electrode disposed on the distal section of the probe and coupled to an energy source to apply energy to tissue inside the body. A plurality of apertures are formed in the electrode. A fluid-directing assembly is disposed in the distal section of the probe having an axial channel that is in fluid communication with at least one trans-axial channel disposed at right angles to the axial channel and leading to an exterior of the assembly. A blocking terminus is disposed forward of the at least one trans-axial channel that prevents irrigation fluid from flowing axially in a forward direction.

According to an aspect of the apparatus, some of the apertures are oriented at a backward angle with respect to the axis of symmetry to deliver the fluid that exits the assembly diagonally behind and outward of the distal section.

According to another aspect of the apparatus, the assembly comprises between two and twelve trans-axial channels.

According to still another aspect of the apparatus, the assembly includes exactly one trans-axial channel.

According to one aspect of the apparatus, the apertures have diameters in a range of 0.05-0.2 mm.

According to a further aspect of the apparatus, the distal section of the probe has a diameter of 2.5 mm.

According to yet another aspect of the apparatus, some of the apertures are oriented at a forward angle with respect to the axis of symmetry to deliver the fluid diagonally forward and outward of the distal section.

According to one aspect of the apparatus, the assembly also includes at least one notch adapted to support a sensor within the lumen of the electrode.

There is further provided according to embodiments of the invention a method for cardiac ablation, which is carried out by introducing a probe into a heart of a subject. The probe has at least one hollow electrode disposed on its distal section, the electrode being coupled to an energy source to apply energy to tissue in the heart. The electrode a plurality of apertures formed through its wall. The method is further carried out by locating the distal section of the probe in proximity to a target in the heart, and thereafter conducting ablation energy via the electrode into the heart to affect an abnormal electrical conduction therein. While conducting ablation energy conveying irrigation fluid into an axial channel of a fluid-directing assembly in the distal section, and directing the irrigation fluid from the axial channel through a plurality of trans-axial channels disposed at right angles to the axial channel and leading to an exterior of the assembly while blocking the irrigation fluid from flowing axially in a forward direction beyond the trans-axial channels.

An aspect of the method is carried out by passing a sensor via the probe onto a support in the assembly, and sensing bioelectric information from the heart with the sensor.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.
System Overview.

Figure 1:
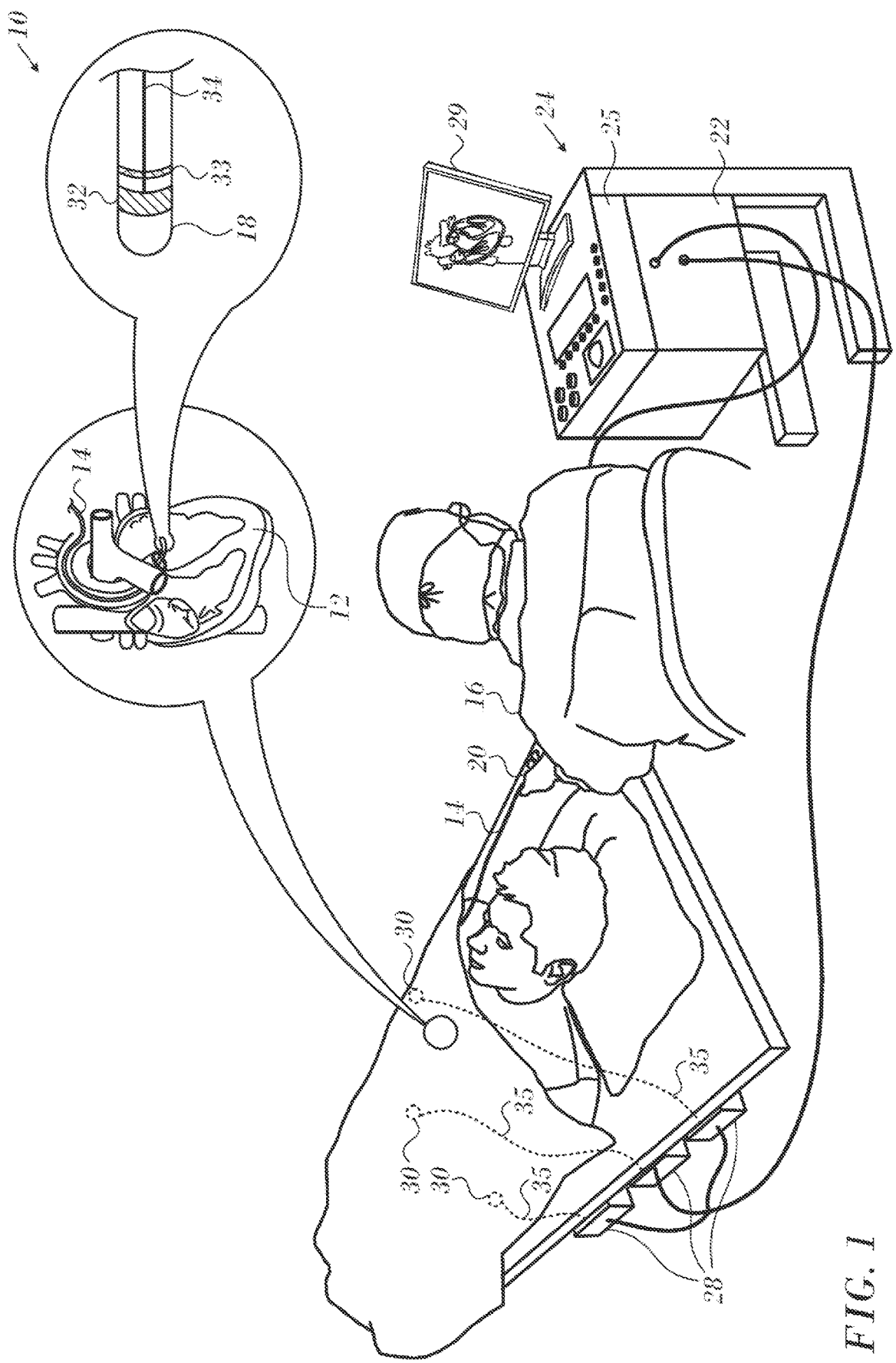
FIG. 1 is a pictorial illustration of a system for performing cardiac ablative procedures in accordance with an embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892, 091, whose disclosures are herein incorporated by reference. One commercial product embodying elements of the system 10 is available as the CARTO® 3 System, available from Biosense Webster, Inc., 3333 Diamond Canyon Road, Diamond Bar, CA 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50°C) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A sensor for bioelectric information, e.g., a temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally applied reference patch attached to the exterior of the subject's body, or on an internally placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

First Embodiment

Figure 2:
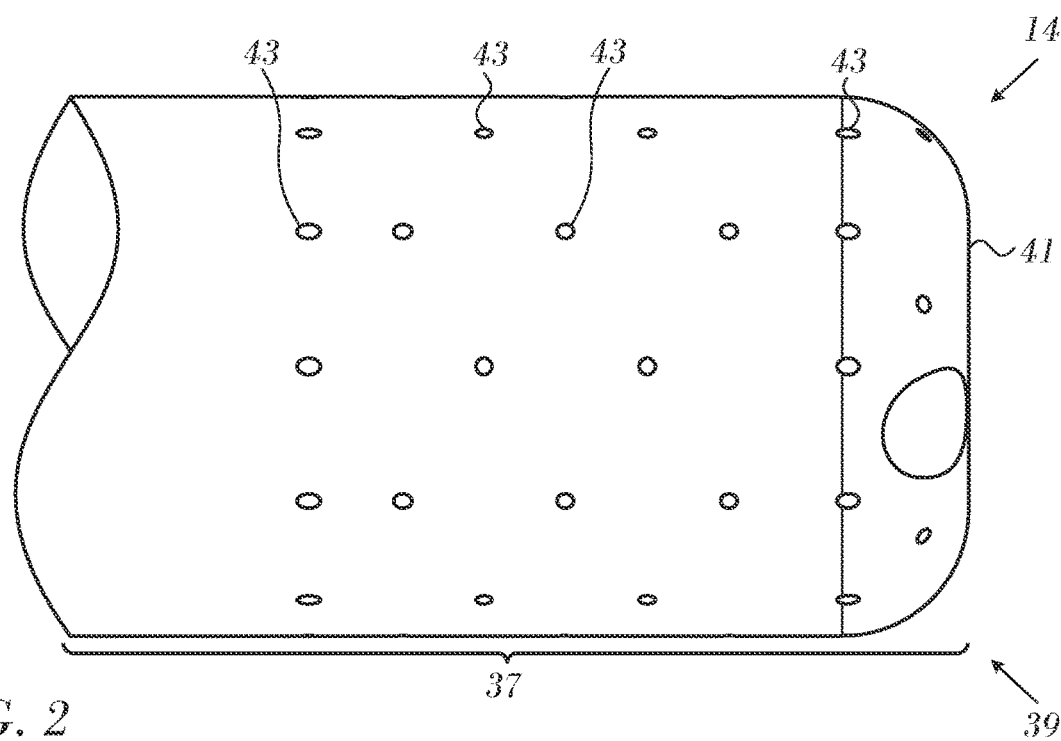
FIG. 2 a side elevation of the distal end portion of a catheter in accordance with an embodiment of the invention.

Reference is now made to FIG. 2, which is a side elevation of distal end portion 37 of a catheter 39 adapted for cardiac ablation in accordance with an embodiment of the invention. The distal end portion 37 is a generally hollow cylinder, having a typical diameter of 2.5 mm. Tip 41 may be electrically conductive and function as an ablation electrode that is linked to a RF current generator. Typically, during ablation, heat is generated through resistive heating of the tissue. The heat conducts to surrounding regions including the ablation electrode. In order to dissipate the heat and dilute the surrounding blood, irrigation apertures 43 or pores are formed in the distal portion 37. The apertures 43 typically have diameters in an approximate range of 0.05-0.2 mm. 0.075 mm apertures are used in a current embodiment. Irrigation fluid is supplied through an internal conduit (not shown) that extends through the lumen of the catheter 39. The rate of flow of the irrigation fluid is controlled by an irrigation module, and typically varies from 2-30 cc per minute but may be higher or lower than this range. A flow rate of 15 cc per minute is suitable for high flow requirements. By varying either or both of the rate of flow and the temperature of the irrigation fluid, the temperature about the distal end portion 37 may be controlled in accordance with the teachings of commonly assigned copending Application Ser. No. 14/860,021, U.S. Patent Application Publication No. 2015/0272667 and U.S. Patent Application Publication No. 2012/0157890, which are all herein incorporated by reference.

Figure 3:
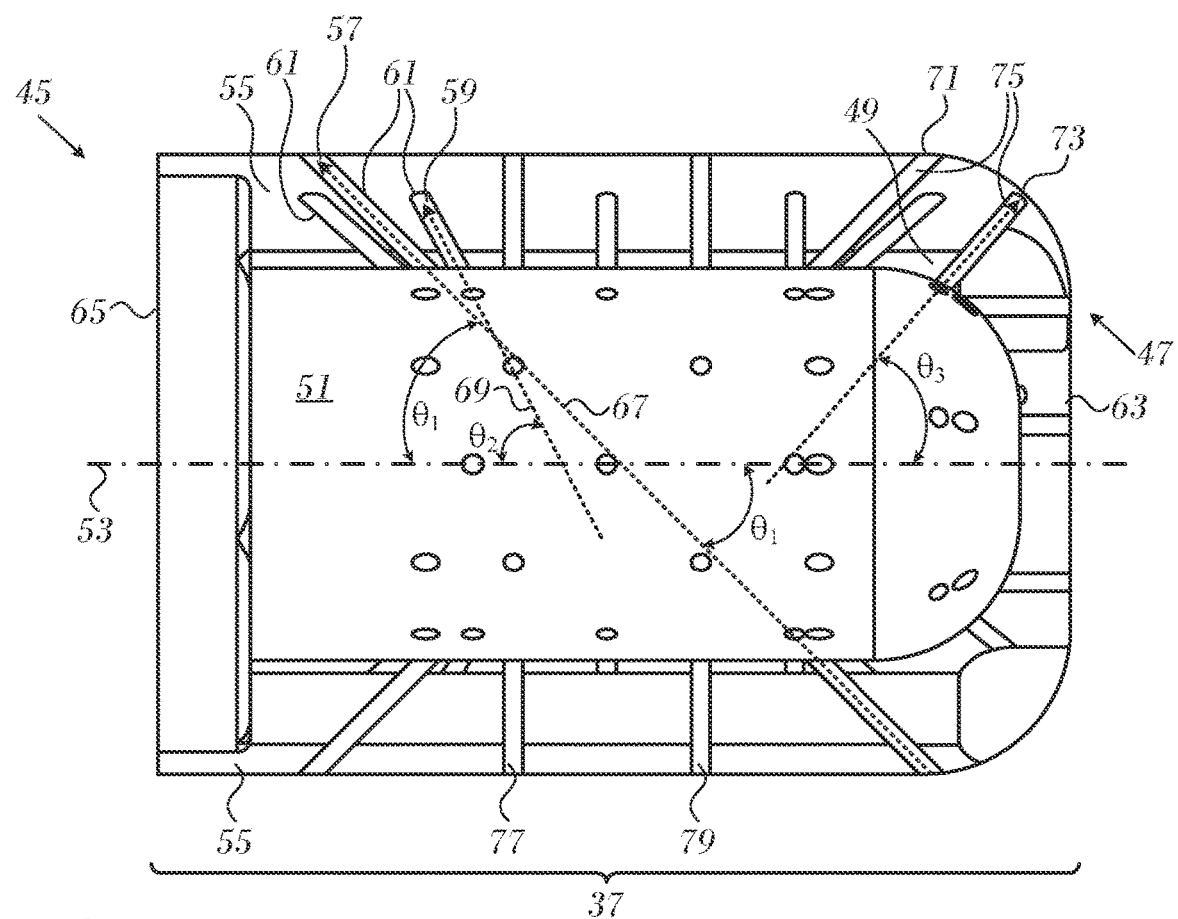
FIG. 3 a longitudinal sectional view of the distal end portion shown in FIG. 2 in accordance with an embodiment of the invention.

Reference is now made to FIG. 3, which is a longitudinal partially cutaway view of the distal end portion 37 of a catheter 45, in accordance with an embodiment of the invention. The distal end portion 37 comprises a hollow electrode 47 having a lumen 49 (best seen in FIG. 4). The lumen 49 is partially occupied by a fluid delivery assembly 51. The distal end portion 37 has a longitudinal axis of symmetry 53. Apertures 57, 59 and other apertures 43 (FIG. 2) are formed in side wall 55 of the electrode 47. The apertures place the exterior of the electrode 47 in fluid communication with the lumen 49 via channels, e.g., channels 61. Channels 61 are directed outward and backward. For purposes of this disclosure, the term "backward" refers to a direction from distal tip 63 generally toward to a proximal end 65 of the distal end portion 37. The term "outward" refers to a direction generally away from the axis of symmetry 53. Longitudinal axes 67, 69 of the apertures 57, 59 intersect the axis of symmetry 53 at angles of incidence $\theta_1$ and $\theta_2$, respectively. The angles of incidence of the outward, backward-directed apertures with the axis of symmetry 53 may vary from 5 to 75 degrees, and are optimally around 45 degrees.

Irrigation fluid is delivered under pressure from an external source through the catheter into assembly 51, The irrigation fluid exits the assembly 51 into the lumen 49 of the electrode 47. The irrigation fluid then exits the lumen 49 via the apertures 57, 59 in directions indicated by arrows in the axes 67, 69. Irrigation fluid so directed cools an area diagonally behind and outward of the distal end portion 37 as further explained below in the discussion of FIG. 7.

Similarly, outward, forward-directed apertures 71, 73 direct the irrigation fluid in directions specified by the angulations of their respective channels 75 with respect to the axis of symmetry 53, e.g., angle of incidence $\theta_3$ in the case of aperture 73 to deliver fluid diagonally forward and outward of the distal end portion 37.

Additionally, the distal end portion 37 comprises conventional sideward directed apertures, e.g., apertures 77, 79, which direct the irrigation fluid outward and sideward from the distal end portion 37.

Figure 4:
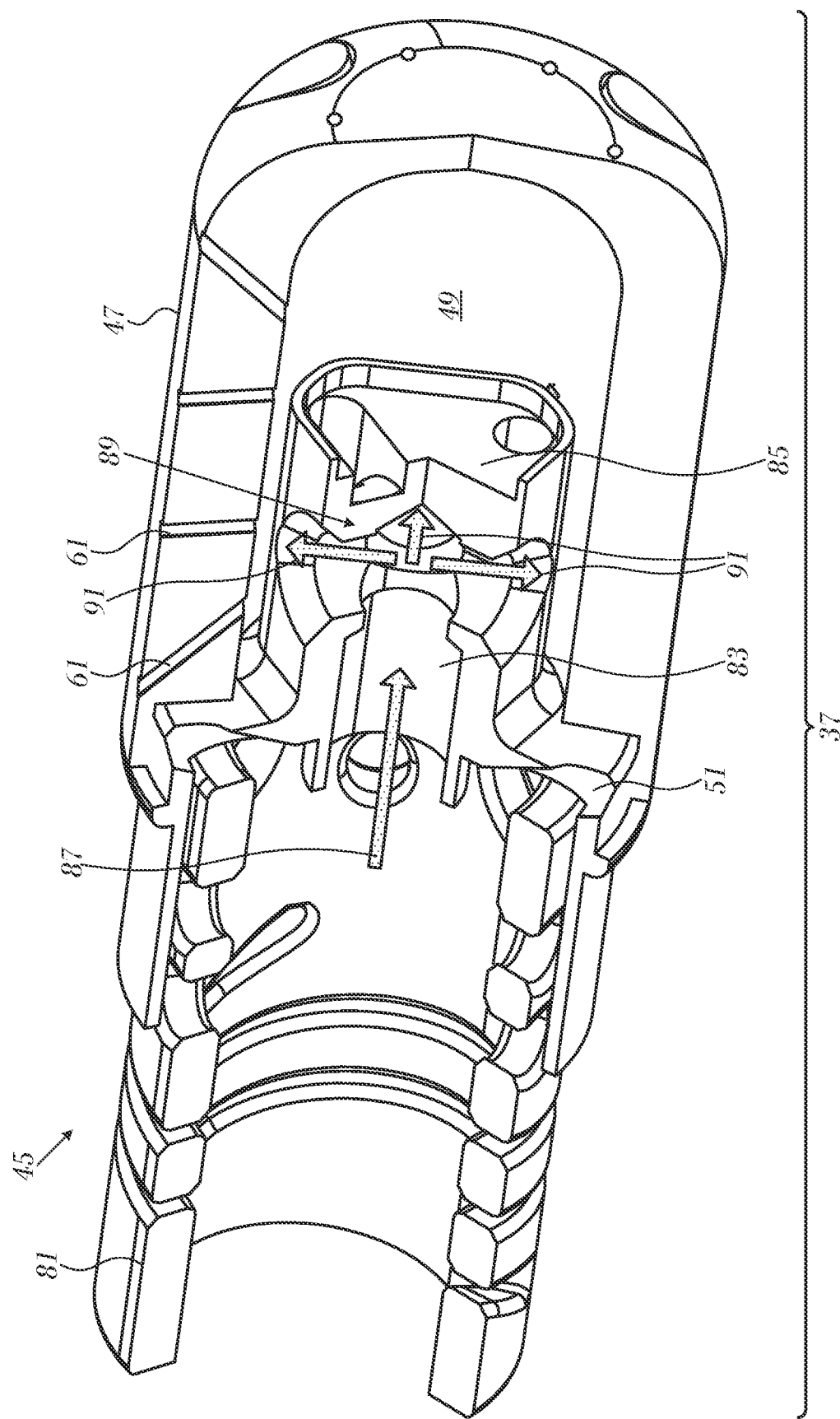
FIG. 4 is a cut-away sectional view of a distal segment of an ablation catheter showing a fluid-directing assembly in accordance with an embodiment of the invention.

Reference is now made to FIG. 4, which is a cut-away sectional view of distal end portion 37 of the catheter 45 in accordance with an embodiment of the invention. Assembly 51 mates with segment 81 of the catheter 45 and with the electrode 47. The assembly 51 comprises an axial lumen 83 that conducts irrigation fluid distally toward a blocking terminus 85 that prevents the irrigation fluid from continuing in a forward direction. The irrigation fluid flow is indicated by an arrow 87. At the terminus 85 a plurality of channels 89 branch trans-axially outward at 90° angles to the axial lumen 83, diverting the flow outward as indicated by arrows 91. The irrigation fluid enters the lumen 49 transverse to the axis of the catheter 45, generally toward the lateral channels in the electrode 47, such as the channels 61.

If the irrigation path exited the lumen 83 in alignment with the axis of symmetry 53 (FIG. 3), irrigation flow through the channels 61 would be disfavored, because the flow would be required to reverse course, and to turn more than 90 degrees to enter the proximally angled channels, such as the channels 61. It is an advantage of the arrangement of FIG. 4 that the irrigation flow is relatively more evenly distributed to all the holes in the electrode 47 than if the flow exited the assembly 51 in a forward direction.

Figure 5:
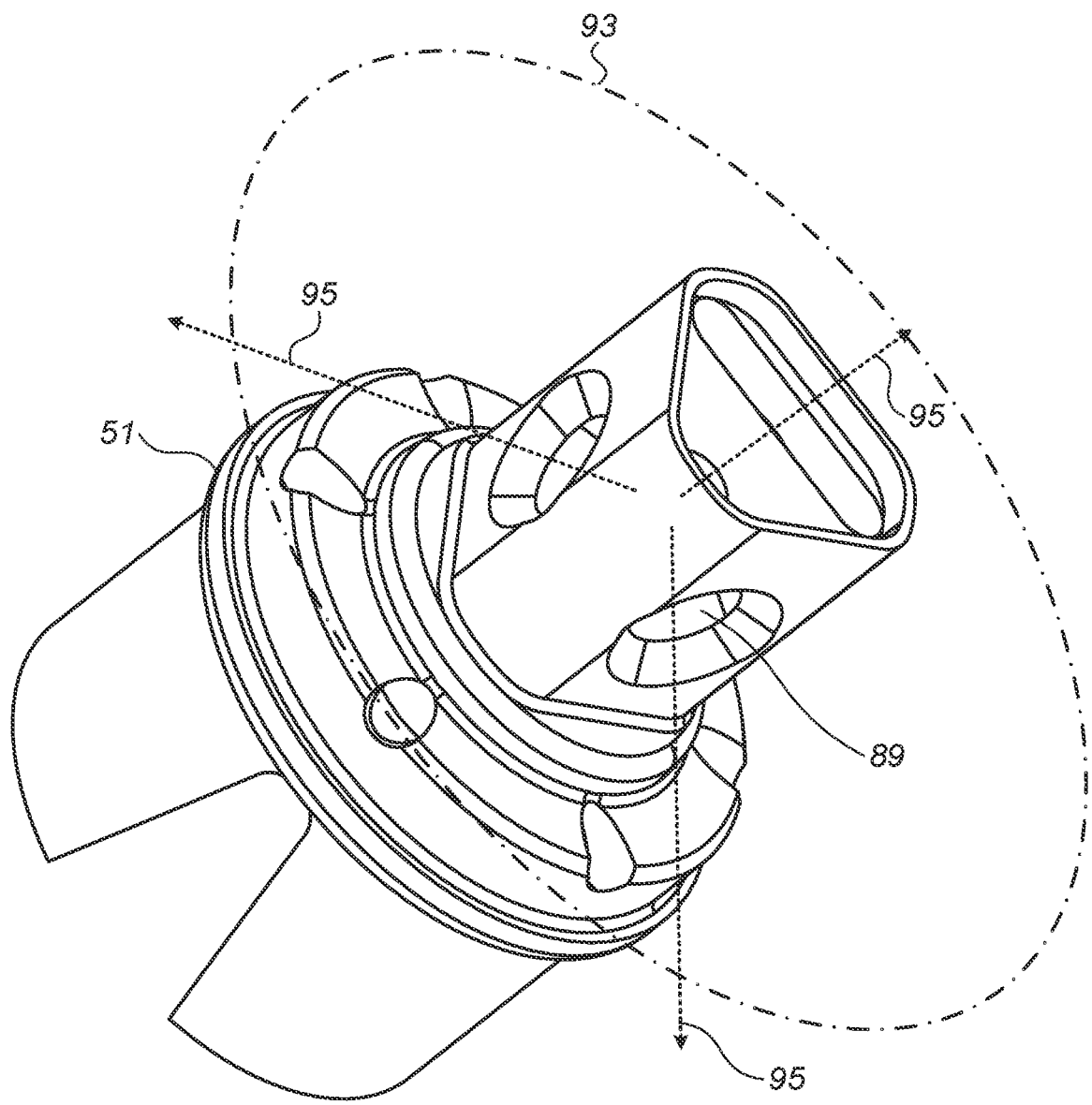
FIG. 5 is an oblique elevation of the fluid-directing assembly shown in FIG. 4 in accordance with an embodiment of the invention.

Reference is now made to FIG. 5, which is an oblique elevation view of the assembly 51 (FIG. 4) showing the channels 89 in accordance with an embodiment of the invention. In this embodiment there are three channels 89, which lie in a plane 93, and are distributed about the axis of the catheter at 120° angles. Direction of flow from the lumen 83 (FIG. 4) to exit the assembly 51 is indicated by broken lines 95. Other embodiments may have a different number of channels 89, typically varying from two to twelve channels.

Figure 6:
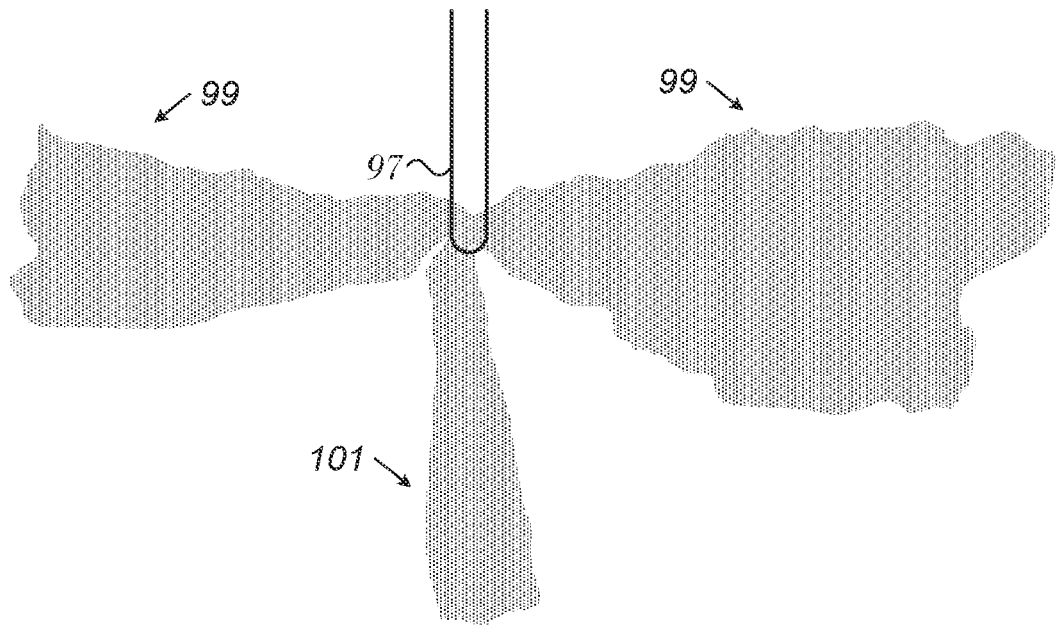
FIG. 6 is a diagram illustrating irrigation flow patterns from a catheter in accordance with the prior art.

Reference is now made to FIG. 6, which is a diagram illustrating irrigation flow patterns from a catheter in accordance with the prior art. A distal end portion 97 comprises conventional sideward directed apertures. Plumes 99 of irrigation fluid are primarily directed outward at 90° to the longitudinal axis of the distal end portion 97. A smaller plume 101 is directed forward of the distal end portion 97.

Figure 7:
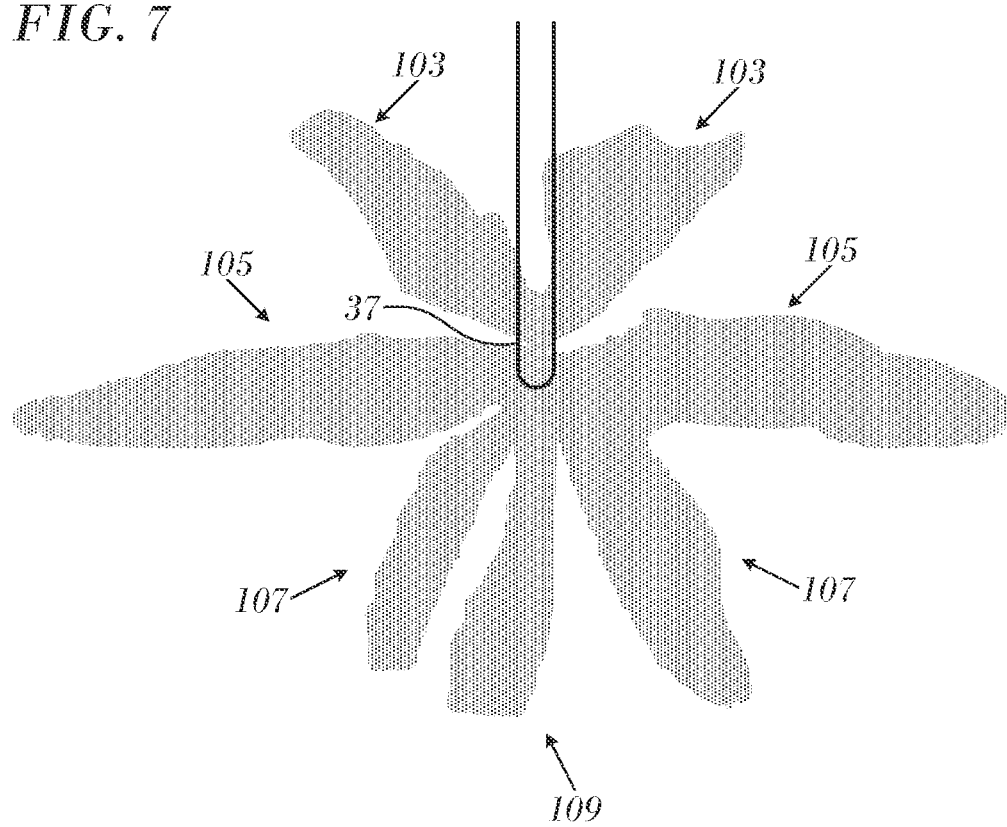
FIG. 7 is a diagram illustrating irrigation flow patterns from a catheter in accordance with an embodiment of the invention.

Reference is now made to FIG. 7, which is a diagram illustrating irrigation flow patterns from a catheter in accordance with an embodiment of the invention. Plumes 103 are directed diagonally backward from distal end portion 37, a feature, which is lacking in the case of FIG. 6. In addition there are plumes 105 directed sideward, plumes 107 directed diagonally forward (lacking in FIG. 6), and plume 109 directed forward of the distal end portion 37.

Second Embodiment

Figure 8:
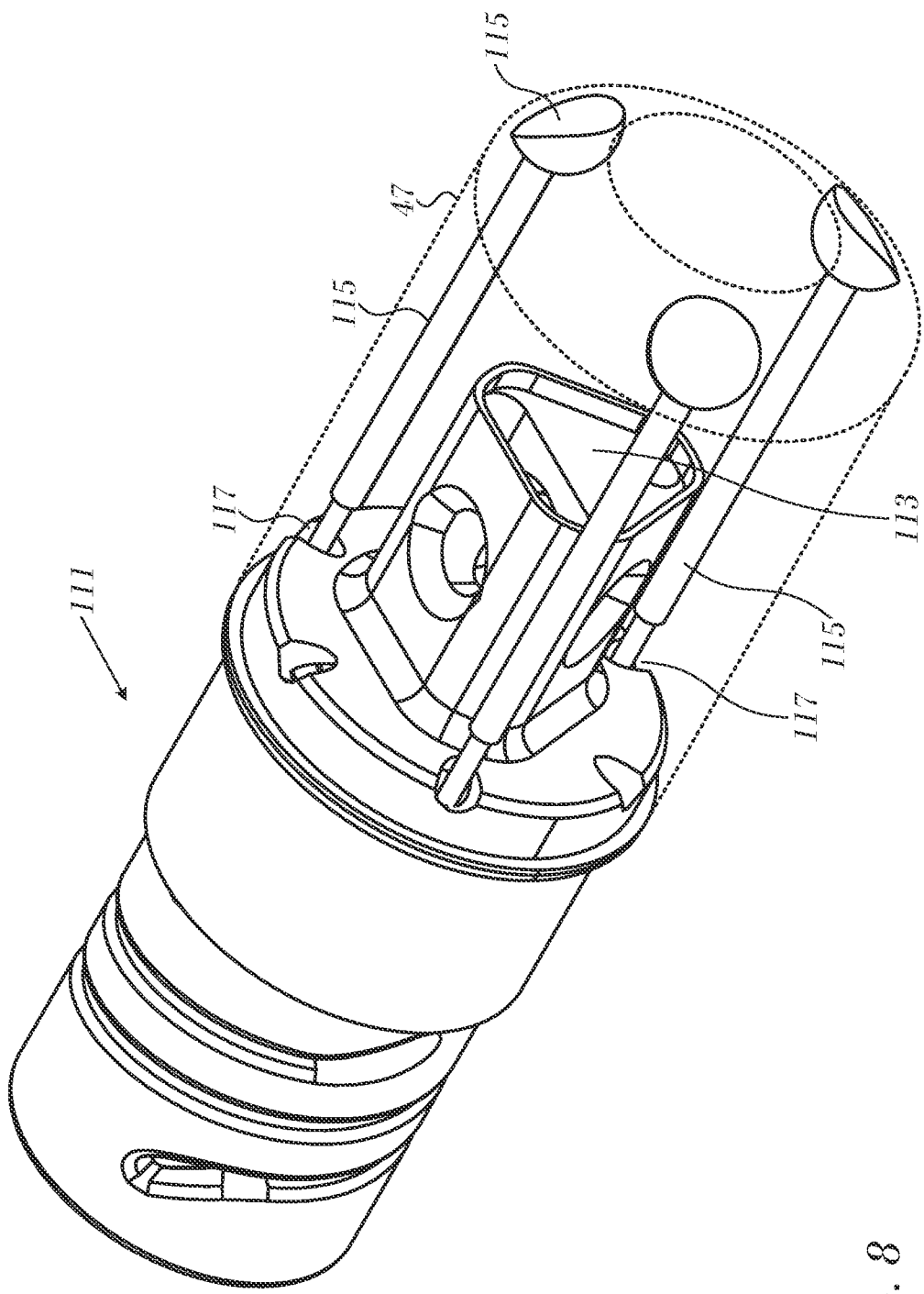
FIG. 8 is an oblique elevation of the distal end of a catheter in accordance with an alternate embodiment of the invention.

Reference is now made to FIG. 8, which is an oblique elevation of the distal end of a catheter 111, in accordance with an alternate embodiment of the invention. Assembly 113 is disposed within electrode 47. In addition to the fluid diversion function described above, the assembly 113 has a second function—supporting sensors 115 through slots 117. The sensors 115 can be any sensor suitable for obtaining electrophysiologic data from the body, e.g., temperature sensors for monitoring tissue ablation. The slots 117 allow passage of the sensors through assembly 113 into the wall cavity of electrode 47. In operation, while the catheter is in the heart, different sensors may be inserted through the catheter through the slots 117 and retracted as dictated by the needs of the medical procedure.

Third Embodiment

Figure 9:
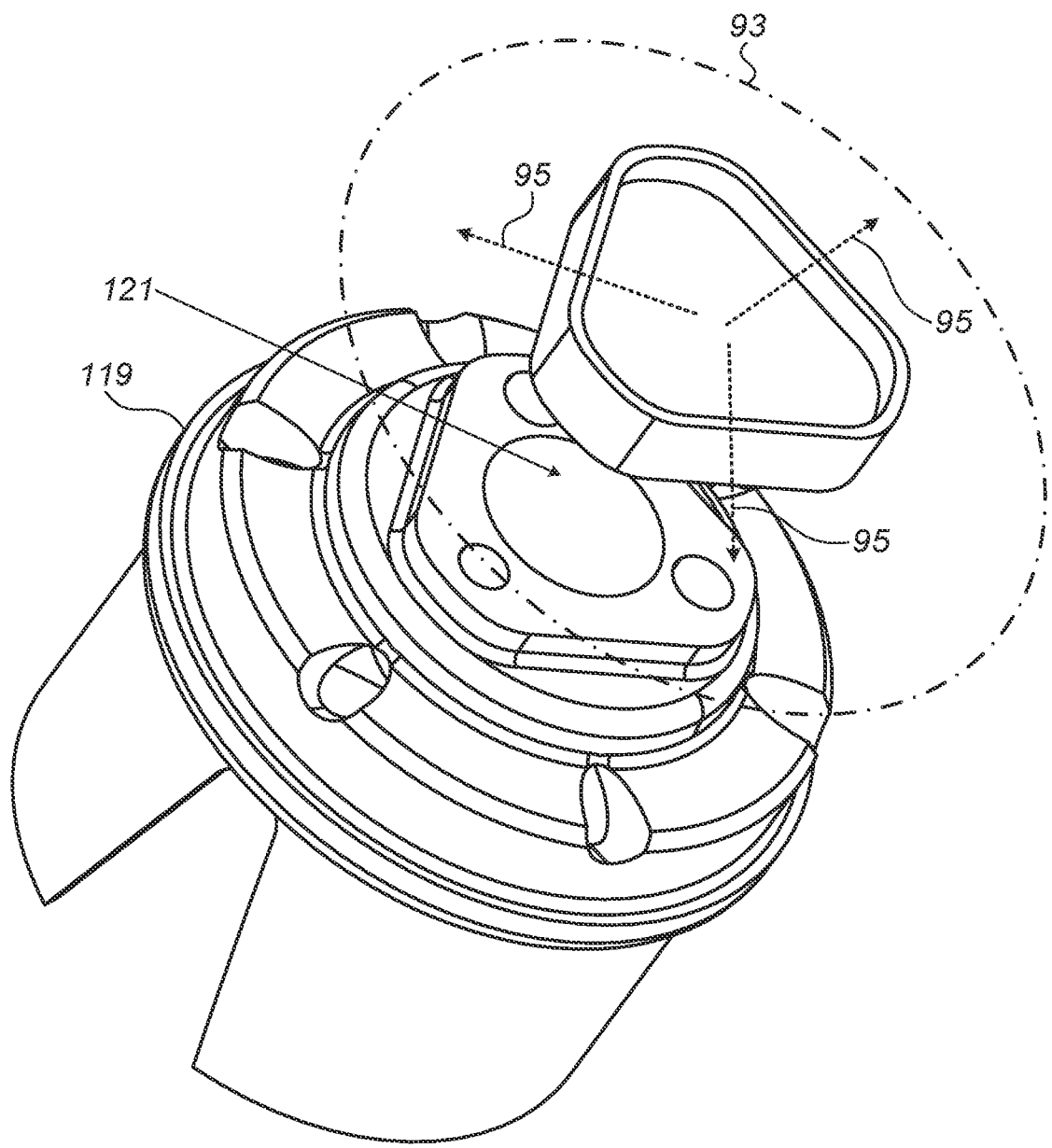
FIG. 9 is an oblique elevation of the fluid-directing assembly shown in FIG. 4 in accordance with an alternate embodiment of the invention.

Reference is now made to FIG. 9, which is an oblique view of an assembly 119, in accordance with an alternate embodiment of the invention. FIG. 9 is similar to FIG. 5, except now there is a single transaxial channel 121 that forms a slot, extending about a sector about the circumference of the lumen 83 that can be 360 degrees as shown in FIG. 9. There may be one slot as shown in FIG. 9. Alternatively more than one slot may be distributed about the circumference of the assembly.

Fourth Embodiment

Figure 10:
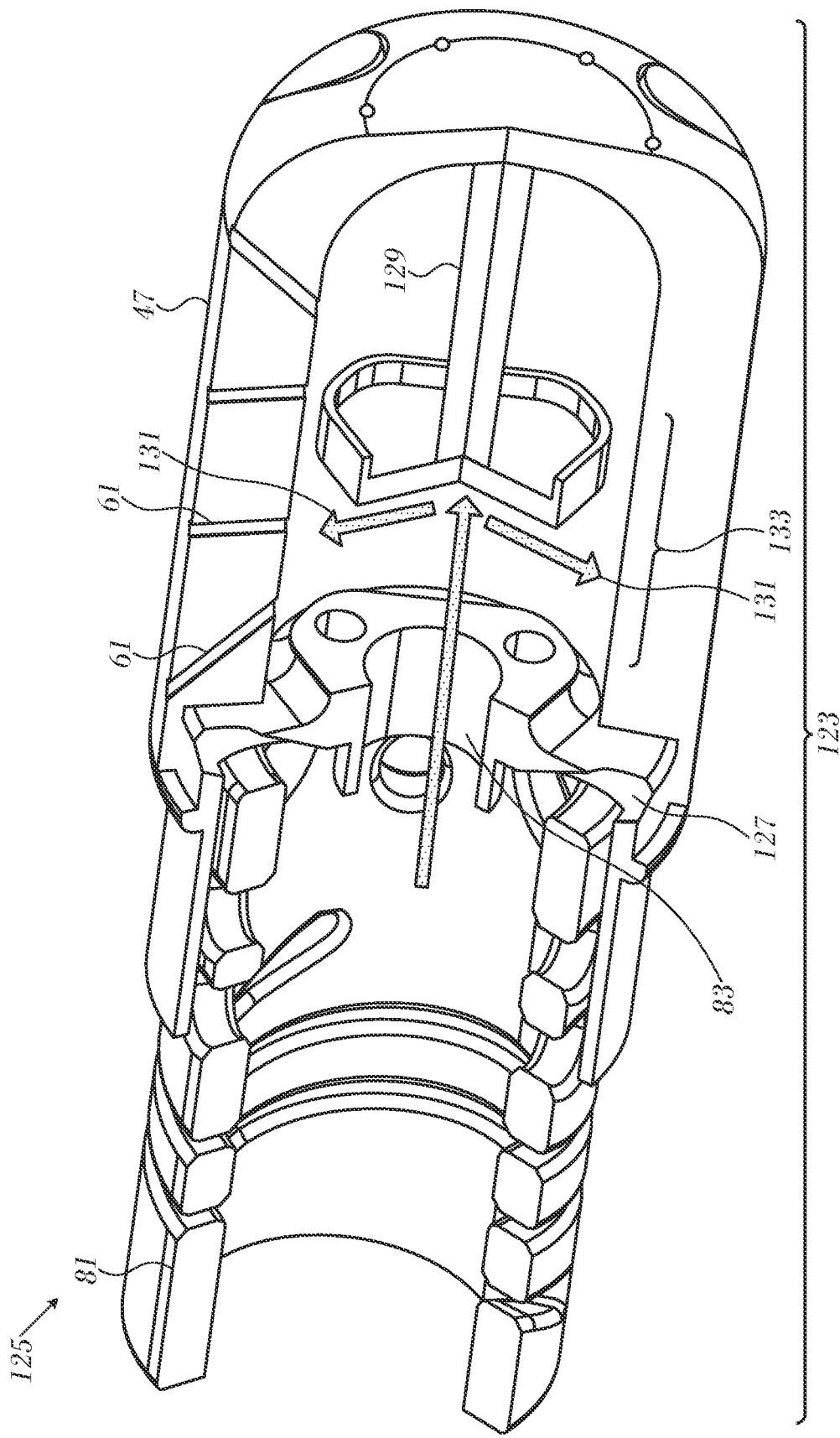
FIG. 10 is a cut-away sectional view of a distal segment of an ablation catheter showing a fluid-directing assembly in accordance with an alternate embodiment of the invention.

In this embodiment a single gap provides flow transverse to the axis of symmetry in a full 360 degree spread. Reference is now made to FIG. 10, which is a cut-away sectional view of distal end portion 123 of a catheter 125 in accordance with an alternate embodiment of the invention. Assembly 127 mates with segment 81 of the catheter 125 and with the electrode 47. Unlike the embodiment of FIG. 4, the assembly 127 lacks the channels 89 and the blocking terminus 85. Instead the flow exits the distal end of the assembly 127 and continues distally within the lumen 49, striking a baffle 129, which is spaced apart from the assembly 127 by a gap 133. The baffle 129 deflects the flow of irrigation fluid transverse to the axis of symmetry toward the wall of the electrode 47 in a 360 degree radial spread, indicated by arrows 131. Thereafter, the irrigation fluid enters the channels 61 and the other channels that penetrate the wall of electrode 47 as described in the discussion of FIG. 4.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A medical apparatus, comprising:
   a probe, having a distal segment section for insertion into a body of a subject and a longitudinal axis of symmetry;
   at least one electrode coupled to the distal segment section of the probe and coupled to an energy source to apply energy to tissue inside the body, the electrode comprising an outer surface, a lumen, and a wall having a plurality of apertures formed therethrough;
   a fluid-directing assembly that mates to the distal segment section of the probe and the at least one electrode, the fluid-directing assembly comprising an axial channel that is in fluid communication leading to an exterior of the fluid-directing assembly and into the lumen of the electrode, and at least three slots disposed radially about the axial channel of the fluid-directing assembly and extending through the fluid-directing assembly parallel to the axial channel;
   a baffle fixed to the electrode and spaced apart from the fluid-directing assembly with a gap between the baffle and the fluid-directing assembly to deflect any flow of fluid transverse to the axial channel; and
   at least three sensors, each sensor extending at least partially through one of the at least three slots formed on the fluid-directing assembly.

2. The apparatus according to claim 1, wherein some of the plurality of apertures are oriented at a backward angle with respect to the longitudinal axis of symmetry to deliver the fluid that exits the fluid-directing assembly diagonally behind and outward of the distal segment section.

3. The apparatus according to claim 1, wherein the fluid-directing assembly comprises between two and twelve trans-axial channels.

4. The apparatus according to claim 1, wherein the fluid-directing assembly comprises exactly one trans-axial channel.

5. The apparatus according to claim 4, wherein the exactly one trans-axial channel extends 360 degrees about the axis of symmetry.

6. The apparatus according to claim 1, wherein the plurality of apertures has diameters in a range of 0.05-0.2 mm.

7. The apparatus according to claim 1, wherein the distal segment section comprises a diameter of 2.5 mm.

8. The apparatus according to claim 1, wherein some of the plurality of apertures are oriented at a forward angle with respect to the longitudinal axis of symmetry to deliver the fluid diagonally forward and outward of the distal segment section.

9. A method to direct irrigation fluid from a medical probe, comprising the steps of:
   providing a probe having a distal segment section, a longitudinal axis of symmetry, at least one electrode disposed on the distal segment section of the probe and coupled to an energy source to apply energy to tissue, the electrode having an outer surface, a lumen, and a wall having a plurality of apertures formed therethrough, and a fluid-directing assembly that mates to the distal segment section and the at least one electrode, the fluid-directing assembly having at least three slots disposed radially about an axial channel of the fluid-directing assembly and extending through the fluid-directing assembly parallel to the axial channel, and at least three sensors, each sensor extending at least partially through one of the at least three slots formed on the fluid-directing assembly;

conveying irrigation fluid into the axial channel of the fluid-directing assembly in the distal segment section; and directing the irrigation fluid from the axial channel through a plurality of trans-axial channels disposed at right angles to the axial channel through the lumen of the electrode and leading to an exterior of the fluid-directing assembly while blocking the irrigation fluid from flowing axially in a forward direction beyond the trans-axial channels by a baffle configured to deflect any flow of fluid transverse to the axial channel.

10. The method according to claim 9, wherein a portion of the apertures are oriented at a backward angle with respect to the axis of symmetry.

11. The method according to claim 10, wherein the plurality of apertures have diameters in a range of 0.05-0.2 mm.

12. The method according to claim 10, wherein the distal segment section comprises a diameter of 2.5 mm.

13. The method according to claim 10, wherein the step of directing the irrigation fluid is performed in a range of 2-30 cc per minute.

14. The method according to claim 10, wherein the step of directing the irrigation fluid is performed in a range of 2-15 cc per minute.

\* \* \* \* \*